United States Patent [19]

Yarush

[11] Patent Number: 4,850,023

[45] Date of Patent: Jul. 18, 1989

[54] UNIVERSAL LISTENING DEVICE

[76] Inventor: Donald J. Yarush, 13826 Little Pond Rd., Valley Center, Calif. 92082

[21] Appl. No.: 945,341

[22] Filed: Dec. 22, 1986

[51] Int. Cl.[4] .............................................. A61B 7/04
[52] U.S. Cl. ..................................................... 381/67
[58] Field of Search ....................... 381/67, 25, 75, 72; 181/158

[56] References Cited

U.S. PATENT DOCUMENTS

| | | | |
|---|---|---|---|
| 2,892,034 | 6/1959 | Fielding, Jr. | 381/67 |
| 2,900,039 | 8/1959 | Burnett | 381/67 |
| 3,247,324 | 4/1966 | Cefaly | 381/67 |
| 3,276,535 | 10/1966 | Shaw | 181/158 |
| 4,438,772 | 3/1984 | Slavin | 381/67 |
| 4,633,498 | 12/1986 | Warnke et al. | 381/25 |

Primary Examiner—Forester W. Isen
Attorney, Agent, or Firm—Brown, Martin, Haller & McClain

[57] ABSTRACT

A listening device for detecting audio frequency sounds and presenting them at increased sound levels to a user's ears. The listening device comprises a lighweight housing with a sound port disposed on a front wall and containing audio processing components for detecting input sound waves, amplifying them, and transferring them to bi-aural sound transfer means coupled to the housing. The bi-aural transfer means directs amplified sound to both ears of a device user simultaneously. The listening device is very lightweight and very compact, with the main housing being less than about 1 cubic inch in volume The listening device employs an acoustical connector on the front wall to allow efficient transfer of sound waves from a series of acoustical adapters, generators, and probes. One such probe is highly useful for automotive engine analysis and another is highly useful for medical applications.

15 Claims, 2 Drawing Sheets

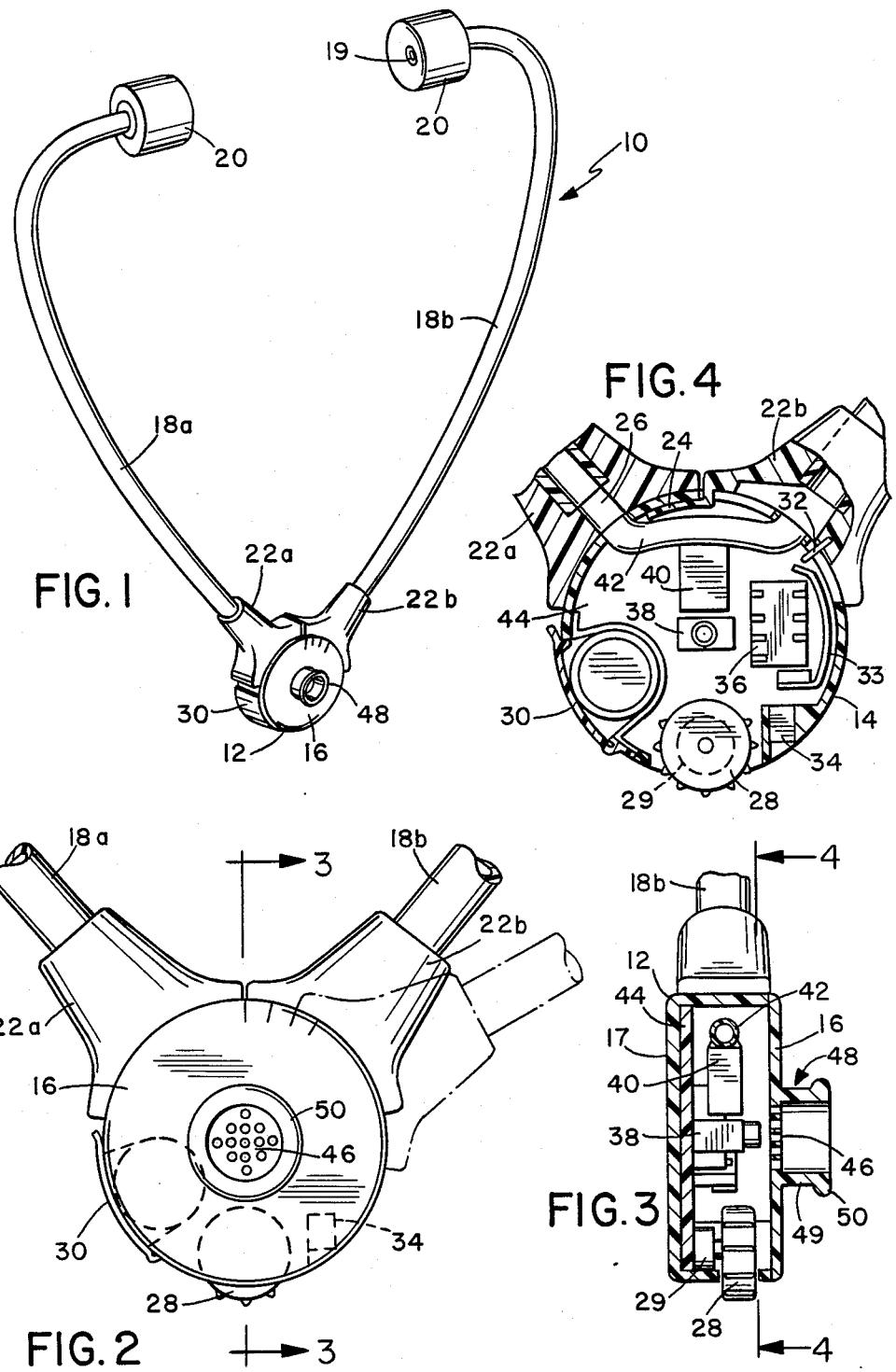

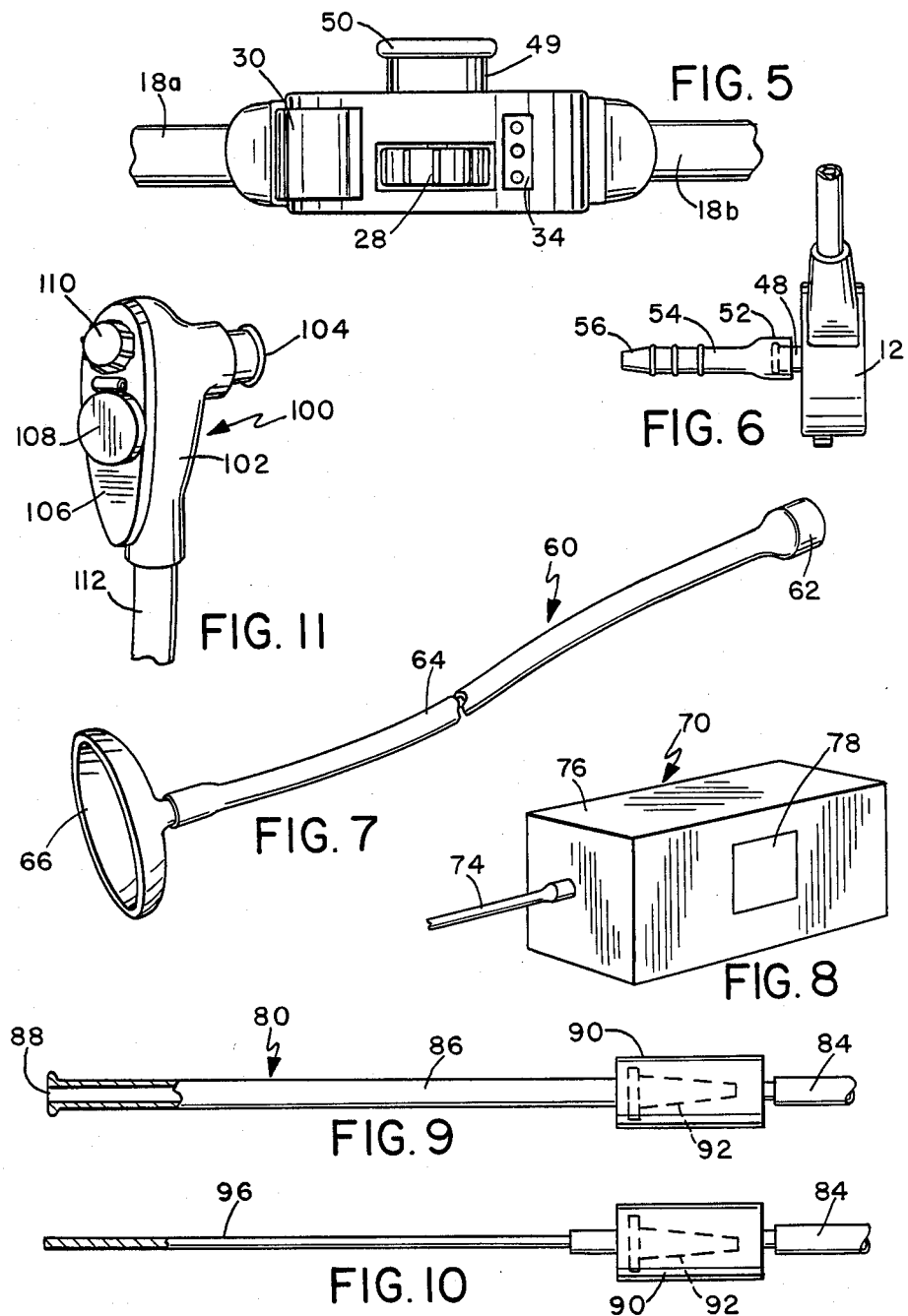

UNIVERSAL LISTENING DEVICE

BACKGROUND OF THE INVENTION

Field of the Invention

This invention relates to apparatus for electronically amplifying sounds and more particularly to a compact, lightweight, apparatus for detecting and amplifying sounds and presenting them through acoustical tubular chambers to both ears of a wearer. The invention further relates to an electronic listening device employing interlocking connectors for coupling an audio amplification portion to a plurality of specialized probes or adapters which interact with sound producing devices, in a variety of audio environments.

Background

In recent years it has been well documented that in excess of twenty-five million people in the United States alone suffer from some form of hearing impairment or loss. While only part of this group suffers a sufficient amount of hearing impairment to be classifiable as being deaf, these statistics do indicate that a large percentage of the population could benefit from some type of hearing assistance device.

Research and technical expertise in the area of aural sensing and amplification has led to the development of a variety of "hearing aid" devices. A major concern and a primary thrust of developing any hearing aid device has been the concept of miniaturization in order to provide for improved aesthetics. Those skilled in the art of hearing aid devices approach development, production or manufacture of such devices with one basic guideline or goal. That goal is that the best, most useful device is one which is very small and is configured to be positioned immediately adjacent to and conformed with, as much as possible, the human ear. This is based on the fact that the hearing aid user typically does not desire to have a hearing aid visible for a variety of aesthetic and psychological reasons.

Over the last few decades this has led to the development of a series of hearing aid devices that slide down inside of the human ear, or have speaker elements that are positioned in the ear with a hearing aid housing that rests above or below the ear, or in fact is incorporated as part of some other device such as the support bar of reading glasses. By designing hearing aid devices to be so small and innocuous, means that the current state of the art hearing aids amplify sounds and present them to only a single ear for sensation by a hearing aid user.

Medical research has shown, however, that a majority of hearing loss or impairment occurs simultaneously in both ears. That is, as a particular individual loses the ability to detect or sense certain audio frequencies or levels, this occurs substantially equally in both ears at the same time. Therefore, providing a hearing aid device that presents improved audio levels to a single ear decreases a users sense of audio balance in perception.

Furthermore, medical research also indicates that the human anatomy, in terms of aural detection, operates by addressing different sound centers on the right and left portions of the brain depending upon whether the sound is sensed by the right or left ear, respectively. Therefore, as the natural ability to present sounds equally to both sides of the brain is lost and a hearing aid is employed to only improve reception by one side, there is a feeling of sensory imbalance which many hearing aid users find irritating and upsetting. Currently, the hearing aid art addresses this problem by providing a second hearing aid for the other ear.

While providing more than one hearing aid seems to be a simple, obvious, and effective approach to solve the abovedescribed problem, it is very expensive and time consuming. Since typical hearing aids cost on the order of $1,000.00 or more, doubling the cost to achieve balanced sensory perception by a user is very expensive. The use of two hearing aids also increases the time required by the end user for achieving a proper sense of hearing by at least double. Now there are two aids which require molding and matching to the individual user along with adjusting frequency ranges, volumes, etc. This is also reflected in the increased cost of preparation and installation.

Users also find that the current technology of hearing aid devices, do not satisfy many of the hearing requirements for applications needed by the user. Even though every attempt has been made to make modern hearing aid devices fairly aesthetic, recent studies have shown that many users of such devices are "part time" users.

Many users find modern hearing aid devices, although beneficial to their hearing, uncomfortable and awkward to use in many situations. Such applications are found in the area of reading books, listening to television, etc. where a person is generally secluded within a home setting and aesthetics is not important, but comfort is. This may also be true of sports related activities, such as golfing, running, etc. where there is also a chance that some devices may be dislodged and become damaged or lost. It is a fairly high price to pay in an activity where hearing is not that important.

Furthermore, while hearing aid devices may satisfy the general audio detection requirements for social events and activities, they do not interface well with many other audio enhancement or production devices. Examples of this latter difficulty are found in attempts to achieve satisfactory results when using hearing aids with audio production equipment utilized for in-flight airline movies, home stereo and computer systems, and some telephone systems.

There are other applications where hearing aids have a tendency to pick up and highly amplify sounds from nearby sources to the exclusion of sounds from more distant sources which the user is trying to distinguish in certain settings. Examples of this could be activities such as theatrical events, stage musical events, plays or similar audience situations where localized audience noise may interferes with perception of more remote stage sounds. The mechanical or electronic hearing aid device cannot be redirected or isolated in the same manner as the human ear naturally functions.

Therefore, it is very desirable to provide an apparatus for improving the detection and presentation of sounds or audio frequencies for a user that does so for both ears simultaneously, in an inexpensive manner, and utilizing an apparatus that can readily interface with existing equipment or devices.

SUMMARY

With the above problems and disadvantages of the present art in mind, it is an object of the present invention to provide an apparatus or device for detecting audio frequency sound waves, amplifying them, and presenting them to both ears of a user simultaneously.

It is a purpose of the present invention to provide a universal listening device capable of interconnecting or being coupled to other audio processing and amplification equipment.

It is another purpose of the present invention to provide improved listening or sound detection for a hearing impaired individual at a lower cost and in an easy to use and comfortable device.

It is a further object of the present invention to provide a universal listening device capable of interconnecting to a plurality of audio probes which are capable of detecting and transferring sounds from a variety of mechanical devices.

It is yet another object of the invention to provide a listening device capable of monitoring pneumatic and hydraulic systems.

It is an advantage of the present invention that it provides a universal listening device which provides balanced aural sensation to a user for a variety of sound detection activities.

These and other objects, purposes, and advantages are realized in a universal listening device which comprises a small lightweight housing having a front wall with a sound port for enclosing and supporting miniature audio processing means and for connecting the processing to a bi-aural sound transfer assembly. The audio processing means comprises electronic components for detecting and amplifying sound waves to a higher power density. A sound detection means is mounted adjacent to the sound port for detecting sound waves and converting them to electrical signals. A very small amplifier connected to the sound detection means increases the amplitude level of the electrical signals and transfers them to a sound generation means for conversion into acoustical waves. A coupling means transfers the amplified acoustical or sound waves into the bi-aural transfer means where they are presented to both ears of a device user simultaneously. The housing also contains or incorporates a power source and volume control means for the amplifier circuitry.

In a further aspect of the invention, the enclosure utilizes a "snap-ring" or similar type of connector element adjacent to and surrounding the sound port. This connector provides for attachment of one end of acoustical transfer tubing to the sound port and acoustical coupling of sound waves to the sound detection means. A variety of sound probes, generators, detectors, convertors, or other sound producing apparatus are connected to the other end of the acoustical transfer tubing providing a variety of sound sources to which a listening device user desires to listen.

In further aspects of the invention, the listening device is constructed to weigh less than about 3 ounces and have a main electronics housing volume less than about 1.0 cubic inches. A series of adapters are provided for connection to the snap-ring connector which interface with, airline audio systems, Infrared audio systems, and engine diagnostic probes. The engine diagnostic probes provide useful information about the status of internal parts and bearing surfaces through detection and presentation of acoustical vibrations. Alternately, a small interface connector allows direct connection of electrical signals to the amplifier.

In a further embodiment of the present invention the housing is configured in the shape of an elongated ellipsoid using a monaural input tubing connector. An output sound port for this housing utilizes the snap-ring connector and is most advantageously coupled to molded ear pieces, stethoscope heads, or similar instruments for medical applications.

BRIEF DESCRIPTION OF THE DRAWINGS

The novel features of the present invention may be better understood from the accompanying description when taken in conjunction with the accompanying drawings, in which like characters refer to like parts and in which:

FIG. 1 is a perspective view of a universal listening device constructed according to the principles of the present invention;

FIG. 2 is a front view of the electronics housing used in the device of the apparatus of FIG. 1;

FIG. 3 is a sectional view of the electronics housing of FIG. 2 taken along line 3—3;

FIG. 4 is a sectional view of the electronics housing of FIG. 3 taken along line 4—4;

FIG. 5 is a bottom external view of the electronics housing of FIG. 2;

FIG. 6 is a side view of the electronics housing of FIG. 2 with an acoustical adapter tube attached;

FIG. 7 is one embodiment of a telephone adapter for use with the device of FIG. 1;

FIG. 8 is one embodiment of an electronic detection type adapter for use with the device of FIG. 1;

FIG. 9 is an acoustical probe for use with engines when coupled to the device of FIG. 1;

FIG. 10 is another acoustical probe for use with engines when coupled to the device of FIG. 1; and FIG. 11 is an alternate housing and coupler assmebly for the device illustrated in FIG. 1 and FIG. 2.

DETAILED DESCRIPTION OF A PREFERRED EMBODIMENT

The present invention comprises a device for detecting audio frequency signals from various sources and converting them to increased audio level output signals for a device user. This is accomplished by employing a small, lightweight "hearing aid" type circuit for detecting and amplifying audio frequency signals. The detection circuit is enclosed in a special housing which supports the circuit and couples output signals generated by the circuit to a bi-aural output transfer means. The bi-aural transfer means couples sound to two curved tubes which project from sides of the electronics package housing and terminate adjacent to and in contact with the human ear of the device user. The electronics package housing incorporates a "snap ring" type connector projecting from a central portion on the face thereof for connection to a series of audio devices or probes.

An improved listening device constructed according to the principles of the present invention is illustrated in perspective in FIG. 1. In FIG. 1, a listening or hearing assistance device 10 is shown having a main electronics housing 12 coupled to right and left user (ear) acoustical transfer or sound tubes 18a and 18b, respectively. It has been found that the use of acoustical transfer tubes 18 improves the sound quality over that of a typical hearing aid. It is believed that the acoustics of tubular chambers contributes to acoustical filtering and frequency shaping or resonant amplification which is perceived as an "improved" sound by a user's aural sensors.

The preferred embodiment of the housing 12 is a generally cylindrical housing having a cylindrical side wall 14 and is closed on each end using front 16 and back 17 end walls, respectively, to complete an acoustically sealed housing. Alternately, the housing 12 can have a square or recti linear shape but circular or elliptical shapes are simpler to manufacture and reduce overall volume. The exact size of the housing is not limited by the present invention but is on the order of 1.5" or less in diameter and 0.75 inches or less in length or thickness in order to provide a light weight device. The housing should be as small as practical with the minimum size being determined by the surface areas required for mounting the transfer tubes 18 and for microphone interface connections as discussed below.

The housing 12 can be made from a variety of materials with a lightweight polymer plastic being preferred. Molded plastics have proven to provide a very cost effective and lightweight housing for the listening device 10. Plastic materials, such as acrylic plastics, allow manufacturing the housing 12 in sub-assembly pieces such as cylindrical sidewalls and shaped end walls which are easily adhered or bonded together along seams to form a single piece housing. The housing is preferably opaque for aesthetic reasons and can be made in any color as the application dictates. Metallic housings allow for anodized and chromed surfaces.

The acoustic transfer tubes 18 can comprise a variety of tubular materials such as, but not limited to, a polyethylene, polymethyl methacrylate, or polyvinyl chloride based plastic. A thin, substantially clear, and rigid plastic tube is preferred for its light weight, low resonant contribution, and generally excellent aesthetic appearance. An exemplary acoustic tube 18 comprises a ¼" outer diameter, thin walled, tube formed from poly methyl methacrylate or similar acrylic plastic. Alternately, the acoustic tubes 18 can comprise other materials such as aluminum or stainless steel which would preferably be anodized, or chrome or plastic coated for eliminating corrosion and improving appearance.

The acoustic tubes 18 extend upward and out from the sidewall 14 of the housing 12 to provide clearance for a users lower face and head over a middle portion of the tube 18 length. The upper portion of the tubes 18 bend toward the user's ears to press against them with sufficient force to assure good aural coupling into the ear or aural canal. The tubes 18 are long enough to allow the housing 12 to be suspended just below the user's chin to provide comfortable use and proper sound "perspective". This makes the tubes 18 about 8 inches in total length. However, an additional separation of about 2 to 6 inches may be preferred for some applications.

An ear plug 19 is mounted on the ends of the acoustic tubes 14 where they contact a user's ears. The ear plugs 19 are molded to have a curved end portion which will fit comfortably in the user's ear without causing undue abrasion. The ends of the ear plugs have an opening which couples sound from the acoustic tubes 18 to each ear. For added comfort and decreased interference from background noise, a foam pad 20 can be placed about the periphery of the ear plugs 19. Such foam pads are known in the art of earphone manufacture and are generally made from a very high porosity plastic material.

A pair of support assemblies or couplers 22 are provided on the sidewall 14 of the housing 12 for mounting the acoustical transfer tubes 18 thereto. The couplers 22 can be formed as an integral part of the side wall of the housing 12 as where the housing is formed from molded plastic, or configured to interlock with or attach to the side of the housing 12.

In one embodiment of the listening device 10, at least one of the support couplers 22 is configured to be movable about a central longitudinal axis projected through the cylindrical housing 12 parallel to the sidewall 14. This is a preferred embodiment because it allows adjustment in the width of the acoustic tubes 18 or ear plugs 19 located thereon, for comfort. Therefore, the listening device 10 better serves the comfort of many users without costly individual fitting or adjustment.

The motion of one support coupler 22 and acoustic tube 18b is illustrated in more detail in the frontal view of FIG. 2. In FIG. 2, the left ear acoustic tube 18b is shown being adjusted over a range of several degrees about the housing 12 central axis. It is estimated that a useful range of 0–15 degrees would allow comfortable adjustment for every user. For ease of use and reproducible results, as where another person adjusts the listening device for the user, a relative position scale or series of marks are placed on the front face of the listening device 10.

An exemplary method of attaching the support coupler 22b to the housing 12 is shown in greater detail in the cutaway view of FIG. 4. In FIG. 4, a base portion of the support coupler 16b extends through an elongated opening in the sidewall of the housing 12 and has a flange or projection 24 which fits under an edge of the opening. This flange hold the base of the coupler 22b against the sidewall 14 as it moves. By making the portion of the coupler base that rests over the outside of the sidewall 14 and the flange 24 large enough with respect to the opening in the sidewall, a large degree of motion is obtained without separation of the support coupler from the housing 12.

The couplers 22 have centrally located cylindrical passages or ports 26 through which sound generated inside the housing 12 is transferred to the acoustic tubes 18. The acoustic transfer tubes 18 are inserted into these passages and secured in place using an adhesive or glue material between the sides of the passages and the tubes 18. The tubes 18 can also be molded into the couplers 22 at the time of the manufacture of the couplers 22, such as where they comprise a molded plastic extension of the housing 12. Alternatively, especially for metallic tubing, threaded sides or flared couplings can be used in cooperation with threads in the support coupler 22 passages 26 to secure the ends of the acoustic tubes 14 in place. These techniques are known in the mechanical arts for joining tubing to a housing and are not described in greater detail here.

For some applications the acoustic tubes 18 can be made to be removable from the couplers 22 as where bayonet, "recess-detent" type, or the above described threaded couplers are used. In these applications, the tubes 18 are manufactured in a variety of colors with a variety of coverings as previously described, or in several lengths, and sold separately or as sets so that a user achieves wardrobe coordination or variation.

As shown in FIGS. 2–5, positioned about the lower periphery of the cylindrical housing 12 is a series of listening device 10 controls and access points useful in the operation of the listening device 10.

One control is a rotary volume control knob or dial 28 which extends through an opening in the sidewall 14. The knob 28 connects to a rotary potentiometer 29 mounted inside of the housing 12 and serves to adjust the volume level for the output of the listening device 10. The impedance value of the potentiometer 29 varies with the specific process module 36 and circuitry employed, but typically is on the order of 25–100k ohms maximum. In the preferred embodiment, the volume control will be labeled with a series of numbers to indicate a relative volume level.

The listening device 10 is powered by a small "hearing aid" type battery inserted into a battery holder 30 which is accessed by a snap open door along the lower edge of the housing 12 in the sidewall 14. The battery is connected to the electronic circuitry of the listening device 10 through an on-off switch which allows the user to save the battery through disconnection. Many hearing aid devices only allow disconnection through battery removal which is inconvenient as well as risky in terms of losing the battery and accidental reverse polarity installation.

For the present invention an automatic "contact" type on-off switch can be mounted within the housing 12 so that its switch contacts 32 and 33 are actuated by one of the support couplers 22. That is, a movable support coupler 22b holds a switch contact 32 for contacting an opposing switch contact 33 within the housing 12. When the acoustic tubes 18 are positioned closest together, the two contacts 32, 33 do not touch. This position is used to disconnect the battery during periods of non-use.

When the tube 18b and the support coupler 22b are moved away from this position, which occurs when a user opens the acoustic tubes 18 farther apart for use, the switch contacts 32 and 33 touch and the battery is connected to the circuit. The interconnecting wires between the switch contacts 32, 33 and the battery are omitted for clarity. This technique provides automatic on-off operation without removal or adjustment of the battery. It will be apparent to those skilled in the art that other types of miniaturized switches and contacts can be employed for automatic activation.

However, for many applications the spacing desired between the acoustic tubes 18 or ear plugs 19 is very close, as where the listening device 10 is used by petite individuals. In this case, extremely narrow tolerances would be needed for the motion of the coupler 22 to activate a switch and not turn off the circuit for a petite user. Therefore, a manually actuated slide or toggle type on-off switch is mounted in the housing 12 along the lower periphery with its actuation lever extending from the underside edge of the housing 12 adjacent to the volume control dial 28. The volume control potentiometer 29 could even employ a switch contact as an integrated component as known in the electronic arts.

The hearing device 10 is configured to interface with various audio frequency generating devices as will be apparent to those skilled in the art from the discussion presented below. However, in passing, it is noted that one method of interfacing with the listening device 10 is through an electrical connection that allows for direct coupling or transfer of electrical signals into the circuitry of the listening device for generation of an audio frequency acoustical output.

This allows higher quality transfer of audio signals through the listening device 10 because it avoids the conversion of electrical signals into sound waves for detection by the microphone 38 and then back to electrical signals. The apparatus for direct connection comprises an interface plug 34 which is mounted along the bottom edge of the listening device 10 adjacent the various controls discussed above.

The main electronic components of the listening device 10 comprise a very small, high quality audio frequency electronic processing module 36, a microphone 38, and a speaker 40. These components represent state of the art miniaturized components which provide high quality sound output in a very small package. For purposes of clarity the specific interconnection or wiring of these components is not shown in FIGS. 3 and 4.

The microphone 38 detects sound waves through a sound port 48 in the front end wall 16 and converts them to electrical signals for further processing. To aid in coupling of the sound waves to the mircophone a tubular sleeve can be employed between the input portion of the microphone 38 and the sound port 48.

An electret type microphone is preferred due to its high sensitivity and relatively flat frequency response over the frequencies of interest. This will require a connection to the battery power source to charge the electret. The microphone must be small enough to fit conveniently in a central portion of the housing 12 and is generally on the order of 0.25 by 0.25 by 0.125 inches in size.

Some exemplary microphones which are commercially available and useful in the manufacture of the present invention are produced by Knowles Electronics of Chicago, Illinois, USA, under the designations of Microphone, Models No. 1842, 1867, or 1984. This type of miniature microphone is well known in the art of hearing aid devices and can be obtained from several commercial suppliers as will be apparent to those skilled in the art of the present invention.

The processing module 36 is connected to the microphone 38 and receives the electrical signals generated by the microphone 38 from detected sound waves. The processing module 36 amplifies the received signals to a higher amplitude or electrical level and couples them to a speaker 40 for conversion to audio frequency sound waves again. The processing module 36 is a miniaturized audio frequency amplifier comprising a series of electronic components disposed on a substrate and encapsulated as an integrated circuit package on the order of 0.25 by 0.25 by 0.125 inches or less in size. The package has appropriate access pins or studs for connection to the battery, microphone, speaker, volume control, auxiliary electronic signal source, and frequency tuning elements.

Some exemplary, commercially available, processing circuits which are useful for the manufacture of the present invention are produced by Knowles Electronics of Chicago, Illinois, USA, under the designations of Integrated Circuit, Models No. LS505, LS505 PLID, LT505, or WV531P. This type of audio circuit is known in the art of hearing aid devices and can be obtained from several commercial suppliers as will be apparent to those skilled in the art of the present invention. The specific electronics module chosen for use in the present invention is determined from operating characteristics, such as available gain and frequency response. It will be apparent to those skilled in the art that a module is chosen using guidelines such as those developed by the hearing aid industry to provide the most satisfactory gain for the particular application.

The electronic processing module 36 provides a high quality sound or audio output in order to provide a user with adequate perception and hearing assistance. The preferred embodiment of the present invention utilizes a processing module whose characteristics, when tested under the ASA STD. 7-1976 (ANSI S3.22-1976) standard used by the hearing aid industry, are approximately:

HF average, Full-on gain: 47 dB
HAIC, Full-on gain: 45 dB

Full-on gain: 51 dB
Maximum Gain: 51 dB
Ref. Test Gain: 42 dB
HF average SSPL-90: 119 dB
Maximum SSPL-90: 125 dB
Maximum SSPL-90 at 1 kHz.: 125 dB
Frequency Response Range in Hz.: 500–4450
Maximum Total Harmonic Distortion at 800 Hz./1600 Hz.: 3%/1%
Maximum Equivalent Noise Input Level: 28 dB The listening device 10 makes use of very small components that have never been mounted in this type of housing or used to establish sound output through bi-aural acoustical tubes. Attempts at hearing assistance devices other, than hearing aids, have used large scale circuit boards or integrated circuits and discrete components to form the processing circuit 36. This creates very large devices on the order of 2 to 3 inches or more square. A larger size means that the listening device would be too heavy for even casual, but frequent, use. The listening device of the present invention uses materials and circuitry that allow a weight of 2 to 3 ounces or less.

The electrical signals processed by the processing module 36 are coupled to the speaker 40 which creates sound waves for transfer through the tubes 18 to a user's ears. The speaker 40 is a small sound generating component approximately 0.375 by 0.25 by 0.1875 inches in size. Exemplary, commercially available, speakers which are useful for the manufacture of the present invention are produced by Knowles Electronics of Chicago, Illinois, USA, under the designation of Receiver, Models No. 1604, 1615, 1915, or 1987.

The speaker 40 is coupled to an acoustic or sound transfer tube 42 which directs sound to the passages 26 in the support couplers 22 for transferring to the acoustic tubes 18. The acoustic transfer tube 42 comprises a tubular material similar to the material chosen for the tubes 18 and is preferably flexible for ease of mounting. The diameter of the transfer tube 42 is approximately the same as the tubes 18 so as to minimize frequency coupling problems. As shown in the side view of FIG. 3, the speaker 40 is placed against one side of the transfer tube 42 and secured in place using a plastic adhesive or similar material.

The specific wiring and interconnection of a processing module 36, microphone 38, and speaker 40 are not illustrated as they vary according to the specific pin arrangement of the module 36. Audio detection and amplification circuits employ input and output points well understood in the art of electronics. Those constructing or using the module 36 would understand where microphone, speaker, switch, and battery connectors must be made. In addition, the manufacturer of a processing module provides a clear indication of what connection pins are used for the microphone, speaker, battery, volume controls and any other components found useful in adjusting the tome or frequency response of the module. Such instructions and other information available in the art make interconnection of the components readily understood by those skilled in the art.

To aide in the construction of the listening device 10 a small circuit board or substrate 46 can be used to mount the components 29, 36, 38, and 40 in place.

The substrate 44 can employ one or more layers of metalization to form the required interconnection paths so that components such as the module 36 and potentiometer 29 can be directly soldered or bonded to connections "pads" on the board. Surface mount technology is well understood in the electronics arts and can be used for some of the components in the listening device 10. Other connections can be accomplished using very fine wire on the order of 28 gauge or smaller.

In any case, the microphone 38 is mounted so that it faces the front end wall 16 of the housing 12 which will face away from the body of a user when the listening device 10 is worn. The microphone 38 is positioned adjacent to a speaker grill, opening, or sound port 46 in the end wall 16 of the housing 12. The opening 46 is naturally required to allow sound to be detected by the microphone 38.

As shown in more detail in FIGS. 2 and 3, the microphone opening 46 is surrounded by a projection or male connector post 48. The connector post 48 comprises a cylindrical side wall 49 having an annular recess, or alternatively a raised edge 50, for mating with a flexible "snap or clip ring" fastener. The "snap-ring" fastener is a type of fastening device known in the mechanical arts for joining a tubular object with a smaller tubular or cylindrical object. The "snap-ring" portion of the connector is tubular member with a side wall having a recess in which a "C-shaped" ring is disposed. The ring subtends a diameter at rest slightly smaller than a cylindrical wall or projection over which it will fit. In this case, the snap-ring (not shown) would encircle a diameter smaller than the raised edge 50. As the tubular member is slid over the post 48, the ring is forced open and the "snaps" closed when slid past the edge 50. The ring is stretched open again with a moderate pulling force.

An alternate embodiment of the listening device 10 would use a "female" "snap-ring" connector which incorporates the "snap-ring" portion in a depression surrounding the microphone opening 46. However, this may be more difficult to make and keep clean when not in use. In addition, other types of connectors such as "bayonnet" or threaded surfaces, but are not as convenient to use.

By placing the microphone in a central location and using the snap connector 48, the listening device 10 advances the art of hearing aid and enhancement devices. The connector 48 allows the user to couple other sound generating or detecting devices into close acoustical coupling relationship with the microphone 38. The microphone 38 will not be offset or blocked by ear molds or the like and can achieve a direct acoustical coupling with the incoming sound. Therefore, the listening device 10 becomes a listening system which improves the hearing of a user in a broader variety of applications than previous devices, especially for the casual user.

The usefulness and advantages of the present invention are further illustrated in FIGS. 6–10 where several interface modules, adapters, or probes are shown for connection to the listening device 10 through the connector 48.

An airline adapter useful for improving sound presentation from headset systems employed in airlines is illustrated in FIG. 6. In FIG. 6, an adapter is illustrated comprising a connector portion 52 having a short length of tubing 54 attached which is connected to a semi-soft rubber coupler 56. The length of the tubing 54 is exaggerated as very short for purposes of illustration. The connector 52 uses a "snap-ring" to secure itself to the male connector post 50 on the listening device 10. The coupler 56 is the type of connector used by the airline industry for headphone sets. It comprises a soft rubber or plastic housing having a series of ridges for engaging the inner diameter of a mating acoustical tube member.

The coupler 56 can also be configured as two separate, or a joined pair of, couplers to engage in a "stereo" sound system as often found in advanced luxury aircraft seating. In this application the coupler 56 acts as a "Y" connector to couple sound into a single input connector 48.

The tubing 54 could be of any suitable length for reaching between the housing 12 and an area adjacent the users waist and could be user adjustable in length as where the connector 52 is removable for cutting the tubing 54. The tubing preferably comprises a soft, flexible material such as a vinyl plastic tubing. This type of adapter can be used for other applications outside of the airline industry where simple acoustical tubing connections are made.

A telephone adapter useful for coupling sound directly to the mircrophone 38 and greatly improving effeciency and volume is illustrated in FIG. 7. In FIG. 7, a telephone adapter 60 is illustrated comprising a connector 62 similar to the previously described connector 52, a length of tubing 64 similar to tubing 54, and a telephone handset coupler 66. The coupler 66 comprises a hemispherical shell or speaker cover having a large enough diameter to allow it to fit over the speaker portion of most telephone handsets. The speaker cover 66 is preferably made of a soft plastic, slightly flexible on the order of 0.25 inches or less thick, to allow it to mold somewhat to the edges of the handset and decrease outside sound penetration into the tubing 64.

The soft plastic also decreases likelihood of damage to equipment or users. For special applications or convenience the coupler 66 is shaped to have a somewhat square cross section at its base in order to provide a tighter fit for some modern telephone handset styles.

Again the tubing 64 comprises one or more premade lengths or is user adjustable such as where smaller lengths incorporate couplers for joining to form a longer length. Along this line the connector 62 can also be configured to allow the tubing 64 to easily separate therefrom for user modifications of length, or cleaning, where desired. Otherwise, the tubing is sealed to the connector 62 as by an adhesive or sealant. At the same time, the end of the tubing 64 where it connects to the coupler 66 can be removable or employ an additional connector where the tubing 64 joins the coupler 66 to allow use of the same tubing 64 for several different couplers and adapters as will be apparent to those skilled in the art from this disclosure.

An adapter 70 which is useful for interfacing with modern sound systems employed by theaters, auditoriums or the like is illustrated in FIG. 8. In FIG. 8., an Infrared (IR) adapter 70 is shown using a connector, not shown, to connect one end of acoustical tubing 74 to the listening device 10. The tubing 74 is connected on the other end to an IR detector/decoder 76.

The IR decoder 76 is an electronic circuit that employs a photo-optical receiver or wave element to detect the presence of IR frequency waves. The detected IR waves are then transferred to a specialized receiver/decoder circuit where various techniques are used to detect the presence of information signals used to modulate the IR frequency waves as a carrier. Since those skilled in the art of electronics and electro-optical design have developed and demonstrated several circuits and techniques for using IR frequency carriers for transmitting information which can be used with the present invention, further details of the detector/decoder 76 are not described in detail here.

A window 78 on one portion of the IR adapter 70 allows IR waves to enter the device from a fixed direction and creates a limited aperture size for any electro-optical detection components. This eliminates cross-talk or interference from nearby systems which are otherwise in a line of sight relationship to the sound system that the user otherwise wants to monitor.

While the adapter 70 has been described as an IR adapter, the principles of the invention are equally applicable to AM and FM radio, or other optical wavelengths, type receivers. It is only necessary that the adapter receive some form of signal which it decodes to generate acoustical waves at audio frequencies that are then transferred along an acoustical transfer or coupling tube to the listening device 10. This is an advantage of the present invention in that it efficiently and inexpensively couples a variety of sound sources, detectors, or generators to a listening device circuit which provides improved sound for a user regardless of the surrounding sound environment.

While the above embodiments have described various apparatus for coupling sound into the listening device 10, the auxiliary connector 34 allows direct interfacing of electronic devices with the listening device 10. Preferably the connector 34 also disconnects the microphone 38 so that extra sound sources are eliminated.

The use of the interface connector 36 allows the listening device 10 to bypass of conversion of electronic signals to acoustical signals and back to electronic signals before re-emerging as acoustical signals. For many applications where the listening device is directly and electronically coupled to sound generation equipment such as stereos, video recorders, etc. this greatly improves efficiency and sound quality.

Some sound systems generate, or are capable of generating electrical signals derived from sound detection or generation apparatus such as microphones, music systems, etc. In this case, the sound generation or reproduction system such as in a theater, lecture hall or classroom, can provide an electrical signal output for use by the listening device 10. In this application a junction box or similar electrical signal transfer means is provided to which a transfer cable is connected on one end. The other end of the cable is connected to the interface plug or connector 34 previously described. This allows direct transfer of the electrical signals in to the processing module 36 where they are processed and transferred to the speaker 42.

While the adapters and decoders described above allow a wide range of improved sound detection schemes, they address the more general "social" or private use of the listening device 10. However, the present invention advances the art of listening devices by virtue of additional applications which are more technical, professional or commercial in use. An example of these types of uses are illustrated in FIGS. 9, 10 and 11, and discussed further below.

Currently, automobile mechanics and similar engine and machinery maintenance personnel use their unaided hearing to detect sounds indicative of abnormal operating conditions. In automobiles, some types of clicking or grinding noises indicate sticky valves or failing bearings. An improved technique used by mechanics has been a rod or tube with a bell on one end for detecting vibrations and sounds where the rod touches the engine. While this does work, it provides crude results and only general information not narrowly defined to specific areas. Also, the general noise level of an operating engine or background environment make accurate or reproducible diagnosis using this technique virtually impossible. However, the present invention allows greatly improved sound detection in this type of application or sound environment.

An apparatus for detecting engine and similar noises using the listening device 10 is illustrated in FIG. 9. In FIG. 9, an engine probe 80 is shown employing a flexible acoustical or sound transfer tubing 84 which uses a snap-ring type connector on one end, not shown, for connection to the listening device 10. The tubing 84 is made of a light weight plastic that is resistant to most solvents for use around engine parts, etc.

Secured to the other end of the tubing 84 is a probe 80 which preferably comprises a metal tube 86 having an outside diameter on the same order as the tubing 84. By using a tubular member 86, vibrations which are converted to sound waves in a hollow passage or probe chamber 88. These sound waves are in turn transferred into the tubing 84 where they are detected and amplified by the listening device 10.

The probe tube 86 is made of metal for purposes of picking up acoustical vibrations efficiently from a component or engine under test. Another rigid material might be used but soft plastics absorb and severly attenuate acoustical vibrations rather than transmit them as sound into the tubing 84.

While the probe tube 86 can couple directly to the transfer tubing 84, the preferred embodiment employs a filter chamber 90 disposed between the probe tube 86 and the transfer tubing 84. The filter chamber 90 comprises a cylindrical plastic or metal housing holding an acoustical filter 92 that filters sound moving into the tubing 84 to restrict the frequencies transferred to the listening device 10. The filter 92 functions analogous to an electronic notch or bandpass filter, severly attenuating any sound above or below predetermined frequency values. For example, the filter 92 can be chosen so that acoustical vibrations or sound below about 500 Hz and above about 7000 Hz are severly attenuated and, therefore, not transferred into the tubing 84. This allows the listening device 10 to receive sound within its range of maximum sensitivity and to block spurious sound that can cause harmonics or resonances and degrade system performance.

The filter 92 comprises a block of porous material such as a ceramic or plastic material used for filtering systems or speaker acoustical covers. There are several materials commercially available which those skilled in the art would readily understand to filter sound. The filter chamber 90 has provision for being opened so that alternate filters 92 can be inserted or removed, and for cleaning when necessary. The filter chamber 90 housing uses a simple slip fitting over which the tubin84 is positioned and can be molded around the probe tube 86 for maximum efficiency.

An alternate embodiment for an apparatus for detecting engine and similar noises using the listening device 10 is illustrated in FIG. 10. In FIG. 10, the engine probe 86 is replaced by a thin solid rod probe 96. The probe proves more useful for some types of applications.

In the automotive testing industry a solid probe 96 proves more useful for detecting noises within the engine block, where as the hollow probe tube 84 is more useful for detecting bearing noises.

While the above apparatus advances the art of mechanical diagnosis, the listening device 10 is not always convenient to use when configured as shown in FIG. 1. Therefore, an alternate embodiment for the electronics housing is illustrated in FIG. 11.

In FIG. 11, an electronics housing 100 is shown using an acoustical transfer tubing 112 from the probe 80, or other acoustical adapters discussed above, connected directly to a lower housing portion 102. The transfer tubing 112 can be secured to a variety of tubular support members or compression fittings which are molded as an integral part of the housing 100.

The housing 100 contains the electronic components, volume control potentiometer, processing module, speaker, and microphone, previously described in relation to the housing 12 and is configured to be a narrow elongated housing slightly larger than the tubing 112 diameter. The housing 100 comprises materials described for the construction of the housing 12.

There is a relatively flat upper housing portion 106 where a battery access cover 108 and a volume control 110 are located. An internal microphone is positioned adjacent to the input point for the tubing 112 so that it is directed to "look" down the tubing. At the same time, a speaker is positioned adjacent to an output port or connector 104. Alternatively, the housing 100 can employ the connector 104 adjacent the internal microphone and the tubing 112 adjacent the speaker.

The connector 104 is either a male or female "snapring" connector as previously discussed in regards to the front end 16 of the housing 12 and the connector 48. The connector 104 allows the housing 100 to be snapped into engagement with acoustical tubing assemblies. In this configuration the listening device 10 can employ a matching female or male snap-ring connector, respectively, on the housing 12 which does not need to contain electronics. In this application, the housing 12 simply conveys sound from the connector 104 to a bi-aural tubing assembly. Therefore, the housing 12 could comprise a cylindrical block of material having a recess for engaging the connector 104 and a central passage with two exit holes for transferring sound to the bi-aural transfer tubes. Alternatively, the connector 104 couples the housing 100 to a monaural housing having a single acoustical passage running between the connector 104 and input acoustical transfer tubing. In this arrangement, a rotary valve may be coupled to the housing 100 and used to select between multiple acoustical inputs.

While the listening device as shown in FIGS. 1-5 is useful for a variety of medical applications it has been found that the configuration using the housing 100 to contain the electronic components and controls 28, 29, 30, 36, 38, and 40 may allow more convenient coupling for additional types of acoustical probes and instruments used in the medical arts. One example is that of the monitor tubing employed by an anesthesiologist during an operation for monitoring heart rate and rhythm, respiratory function, and other vital signs.

It is common for an anesthesiologist to employ one or more specially fitted ear pieces to which the monitor tubing is connected. Unfortunately during an operation the general noise level, plus incidental contact with the monitor tubing cause problems with adequate sensing of the heart tones and respiration. Using the present invention greatly improves the capability to adequately and accurately monitor a patient's condition by amplifying the heart tones.

In this application, an ear piece or form which has been molded to fit the anesthesiologist's ear has a central acoustical passage molded or drilled therein for transferring sound to the ear. A small volume adjacent to and surrounding this passage is hollowed out and a female type snap-ring connector inserted. The female connector can be installed after the fact by using various adhesives, bonding agents, or molding compounds which allows retroactive adaptation of the present invention to existing ear pieces. Alternatively, when a new ear piece is made the connector is inserted into the mold material, which usually comprises a polymer compound, and made a permanent part of the ear piece as the material sets. Therefore, the anesthesiologist now has the ability to use controlled, amplified sound to adequately monitor a patient's heart tones. It has also been found that positioning the electronics housing 100 along, the input monitor tubing at some distance from the ear piece can provide an improved sound quality and ease of control. This takes advantage of acoustical properties of monitor tubing similar to the transfer tubing 18 discussed earlier.

In addition, other forms of sound probes such as used in the recently developed area of auscultation and audio detection which is used for monitoring musco-skeletal acoustical patterns. In this application a soft flexible shroud is placed over a joint to be monitored and a very sensitive microphone or probe used to detect sound produced during joint flexure or rotation. The housing 100 can be coupled to such a shroud in order to amplify the sound detected.

The above embodiments have been described using a single electronics module 36, microphone 38, and speaker 40 for sound reception and generation. However, using the principles of the present invention, the listening device 10 also advances the art because it can accommodate two processing modules 36, microphones 38, and speakers 40, in addition to tone and balance controls (not shown). By positioning the microphones at slight outward angles from each other, the user can receive a greater sense of sound directionality in perception.

In this embodiment, two processing modules 36a and 36b are mounted on the support substrate 44. The two microphones 38a and 38b are positioned adjacent to, and offset from, the center of the housing 12 or front end wall 16 by an equal distance. Preferably two separate sound ports or openings 46 and connectors 48 are used but this is not required for operation of the invention. A single large port 46 and connector 48 will automatically couple sound from the adapters previously described to both circuits simultaneously without need for "Y" connectors or the like.

However, if some directionality or other right/left differentiation is desired, a separate port should be employed for each microphone 38. The microphones should also slant away from each other slightly in order to affect further differentiation of sound direction. Additionally, or in the alternative, a sound shield member such as a cylindrical wall could be placed around, or a flat plate placed between, the microphones 38a and 38b.

The volume control can use a "ganged" pair of potentiometers 29a and 29b or separate controls as room permits in the housing 12. Additional potentiometers can be connected to and between the processing modules 36 to affect "balance" or "tone" control. The connection of these components is accomplished in the same manner as would be done in the stereo and electronics arts for other sound generation circuits as will be apparent to those skilled in the art of the present invention and is not, therefore, described in further detail here.

If two separate channels of sound are to be maintained, the transfer tube 42 must be segmented into two separate tubes 42a and 42b for transferring the sound output from the two processing modules 38a and 38b into the acoustical tubes 18a and 18b, respectively. This can be accomplished by using two tubes or by obstructing the center of a single tube 42, such as with a plastic cement or polymerizing material, and securing the speakers 40a and 40b on opposite sides of this obstruction.

What has been described then is a new type of listening device which provides improved sound reception and perception in a variety of sound environments and does so in a low cost, light weight, aesthetic manner which is especially adapted to occasional or periodic use.

It will be apparent to those skilled in the art that other variations such as curved surfaces for the sides of the housings 12 and 100; colors or decorations impressed on the sides of the tubes 18 or tubing 54, 74, and 84; or additional battery and power source connectors can be employed without deviating from the teaching of the present invention.

The foregoing description of preferred embodiments has been presented for purposes of illustration and description. It is not intended to be exhaustive nor to limit the invention to the precise form disclosed, and many modifications and variations are possible in light of the above teaching. The embodiments were chosen and described to best explain the principles of the invention and its practical application to thereby enable others skilled in the art to best utilize the invention in various embodiments and with various modifications as are suited to the particular use contemplated. It is intended that the scope of the invention be defined by the claims and their equivalents.

What I claim is:

1. A listening device for detecting audio frequency sounds in an environmental volume adjacent to the listening device and presenting the detected sounds at an increased sound level or power density to the ears of a device user, comprising:

a lightweight cylindrical housing, having a cylindrical sidewall about 1.0 inch or less high, with at least two sound transfer ports disposed on said sidewall less than 180 degrees apart and generally circular front and back end walls with a diameter of about 1.5 inches or less, said front end wall having at least one sound input port disposed in a central location thereon;

first and second hollow tubular members having first and second ends, each of said first ends connected to one of said sound transfer ports, said tubular members extending outward from said housing in an arcuate shape so as to place said second ends adjacent a device user's ears, and having ear plug adapters on said second ends for interfacing with the user's ears;

acoustical connection means disposed about said sound input port for releasably connecting one end of acoustical transfer tubing to said sound input port;

audio processing means disposed within said housing for detecting input sounds and amplifying them to have a higher power density than when detected, comprising:
- at least one sound detection means mounted adjacent said front wall sound port for detecting said sounds and converting them to electrical signals whose amplitudes correlate to relative amplitudes of said detected sound waves;
- at least one amplification means mounted within said housing and connected to said sound detection means for increasing the power level of said electrical signals;
- at least one sound generation means connected to said amplification means for generating audio frequency output sound waves from said amplified electrical signals; and
- coupling means disposed within said housing and connected between said sound generation means and said hollow tubular members for coupling sound therebetween.

2. The listening device of claim 1 wherein the combined weight of said lightweight housing, audio processing means, acoustical connection means, hollow tubular members, and coupling means is less than about 3 ounces.

3. The listening device of claim 1 further comprising electrical interface means connected to said amplification means for coupling electrical signals representative of audio frequency sound waves into said amplification means for further amplification and processing.

4. The listening device of claim 1 further comprising acoustical transfer tubing having a first end releasably mountable on said connection means and a second end connected to an audio adapter means, comprising:
- a flexible cylindrical body formed from an outer wall encircling an inner acoustical passage and a plurality of ridges located along a length of the outer wall, said ridges configured to frictionally engage an inner wall of a tubular output connector for a sound wave generating system.

5. The listening device of claim 1 wherein said sound port comprises a raised annular ridge on a cylindrical body for engaging a snap ring fitting.

6. The listening device of claim 1 further comprising acoustical transfer tubing having a first end releasably mountable on said connection means and a second end connected to an engine probe means for contacting surfaces of operating engines and acoustically generating sound waves from vibrations present in said surfaces.

7. The listening device of claim 6 wherein said engine probe comprises a tubular member having a centrally located passage therein for generation of acoustical waves from vibrations in said surface and for transfer of said acoustical waves to said acoustical transfer tubing.

8. The listening device of claim 6 wherein said engine probe comprises a thin solid rod.

9. The listening device of claim 6 further comprising acoustical filter means disposed between said acoustical transfer tubing and said engine probe means for providing frequency filtering of sound waves transferred to said transfer tubing.

10. The listening device of claim 1 wherein said coupling means comprises a flexible coupling tube connected on a first end to said first tubular member and on a second end to said second tubular member and has a small sound port disposed along its length for receiving output from said at least one sound generation means.

11. The listening device of claim 10 wherein said coupling means comprises a Y-shaped flexible coupling tube connected on a first end to said first tubular member and on a second end to said second tubular member and on a third end to said at least one sound generation means.

12. The listening device of claim 1 wherein said sound transfer ports comprise:
- a pair of spaced apart mounting apertures in said sidewall;
- a pair of support bases, each having a hollow passage extending therethrough and radially outward from said housing, said passage configured for mounting a hollow tubular member therein, each support base having a lower footing extending through a mounting aperture;
- at least one footing having a recess abouts its periphery for slidably engaging edges of one mounting aperture and interlocking said footing against said sidewall in sliding engagement; and
- said one mounting aperture being elongated over at least 15 degrees of arc to allow movement of said at least one footing and associated support base over 15 degrees of arc along said sidewall.

13. The listening device of claim 12 further comprising:
- first electrical contact means secured to said at least one footing; and
- second contact means mounted adjacent a travel path of said first contact means in said housing for providing an electrical path when contacted by said first contact means for activating said device.

14. A listening device for detecting audio frequency sounds in an environmental volume adjacent to the listening device and presenting the detected sounds at an increased sound level or power density to an acoustical transfer tube, comprising:
- a lightweight elongated ellipsoidal housing, having first and second ends and a sidewall disposed therebetween;
- a sound input port mounted on said first end for coupling to an acoustical transfer tube;
- a sound output port disposed on said sidewall adjacent to said second end for transferring sound waves from the inside of said housing to second acoustical transfer means;
- a cylindrical quick release acoustical connector disposed about each of said sound ports for releasably connecting acoustical transfer tubing to said ports;
- audio processing means disposed within said housing for detecting input sounds at audio frequencies and amplifying them to have a higher power density than when detected, comprising:
- sound detection means mounted adjacent said input port for detecting said sounds and converting them to electrical signals whose amplitudes correlate to relative amplitudes of said detected sounds;
- amplification means mounted within said housing and connected to said sound detection means for increasing the power level of said electrical signals;
- sound generation means connected to said amplification means for generating audio frequency output sound waves from said amplified electrical signals; and
- coupling means disposed within said housing and connected between said sound generation means and said output port means for transferring sound waves into said second transfer means.

15. The listening device of claim 14 further comprising a molded ear piece connected to said second acoustical transfer means, said ear piece being molded to fit a particular listening device user's ear and having a passage therethrough between said second transfer means and the inner ear portion of the user's ear, and said ear piece having a quick release coupler disposed adjacent said passage between said second transfer means and said ear piece.

* * * * *